United States Patent [19]

Bille et al.

[11] Patent Number: 4,907,586
[45] Date of Patent: Mar. 13, 1990

[54] METHOD FOR RESHAPING THE EYE

[75] Inventors: Josef F. Bille, Rancho Santa Fe; Stuart I. Brown, La Jolla, both of Calif.

[73] Assignee: Intelligent Surgical Lasers, San Diego, Calif.

[21] Appl. No.: 176,230

[22] Filed: Mar. 31, 1988

[51] Int. Cl.$^4$ .............................................. A61N 5/06
[52] U.S. Cl. ........................................ 606/5; 128/395
[58] Field of Search ................ 128/303.1, 395, 347, 128/398, 898

[56] References Cited

U.S. PATENT DOCUMENTS

| | | | |
|---|---|---|---|
| 3,769,963 | 11/1973 | Goldman et al. | 128/303.1 |
| 4,309,998 | 11/1982 | Aron nee Rosa et al. | 128/303.1 |
| 4,391,275 | 7/1983 | Fankhauser | 128/303.1 |
| 4,503,854 | 3/1985 | Jako | 128/303.1 |
| 4,538,608 | 9/1985 | L'Esperance, Jr. | 128/395 |
| 4,559,942 | 12/1985 | Eisenberg | 128/303.1 |
| 4,561,436 | 12/1985 | Munnerlyn | 128/303.1 |
| 4,580,559 | 4/1986 | L'Esperance | 128/303.1 |
| 4,598,311 | 7/1986 | Bellina | 358/93 |
| 4,601,288 | 7/1986 | Myers | 128/303.1 |
| 4,665,913 | 5/1987 | L'Esperance, Jr. | 128/303.1 |
| 4,669,466 | 6/1987 | L'Esperance | 128/303.1 |
| 4,704,583 | 11/1987 | Gould | 330/4.3 |
| 4,718,418 | 1/1988 | L'Esperance | 128/303.1 |
| 4,732,148 | 3/1988 | L'Esperance, Jr. | 128/303.1 |
| 4,770,172 | 9/1988 | L'Esperance, Jr. | 128/303.1 |
| 4,773,414 | 9/1988 | L'Esperance, Jr. | 128/303.1 |
| 4,784,135 | 11/1988 | Blum et al. | 128/303.1 |

FOREIGN PATENT DOCUMENTS

87/07165 12/1987 World Int. Prop. O. ........... 128/395

OTHER PUBLICATIONS

"Ophthaline Lasers," by F. L'Esperance; The C. V. Mosby Company, St. Louis, Toronto, London, 1983, pp. 529–538, 554.
"FM-Laser Operation of the Nd:YAG Laser," by Kuizenga et al., IEEE Journal of Quantum Electronics, Nov. 1970.
"Laser Interactions With the Cornea," by Krauss et al., Survey of Ophthalmology, Jul.-Aug. 1986.
"Noncontact Trephincation of the Cornea Using a Pulsed Hydrogen Fluoride Laser," by Loertscher et al., American Journal of Ophthalmology, Nov. 1987.
"Room-Temperature 2 um HO:YAG and 3 um ER:YAG Lasers," by Huber et al., to be published in Journal de Physique.

Primary Examiner—Lee S. Cohen
Assistant Examiner—David Shay
Attorney, Agent, or Firm—Nydegger & Harshman

[57] ABSTRACT

A method for modifying tissue with a quasi-continuous laser beam to change the optical properties of the eye comprises controllably setting the volumetric power density of the beam and selecting a desired wavelength for the beam. Tissue modification is accomplished by focusing the beam at a preselected start point in the tissue and moving the beam's focal point in a predetermined manner relative to the start point throughout a specified volume of the tissue or along a specified path in the tissue. Depending on the selected volumetric power density, the tissue on which the focal point is incident can be modified either by photoablation or by a change in the tissue's visco-elastic properties.

69 Claims, 3 Drawing Sheets

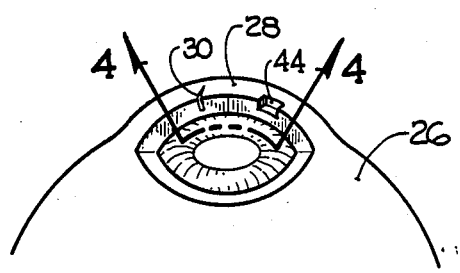
*F*IG.3
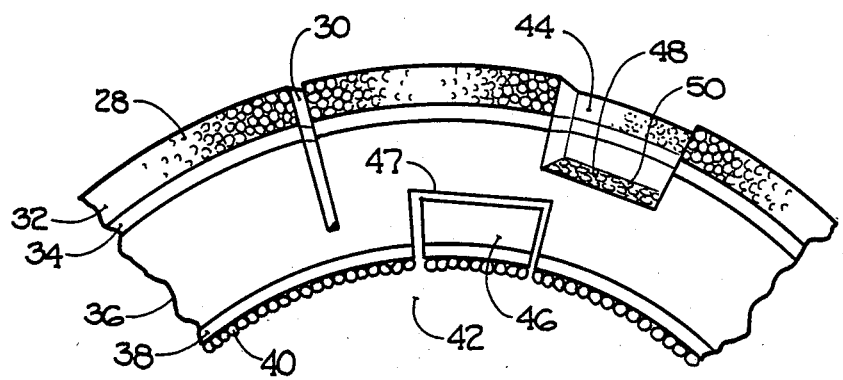
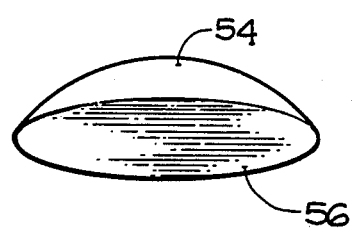
*F*IG.4

METHOD FOR RESHAPING THE EYE

BACKGROUND OF THE INVENTION

The present invention relates generally to methods and procedures for modifying tissue with a laser beam to change the optical properties of the eye. More particularly, the present invention relates to a method for modifying eye tissue by either photoablation or changing the visco-elastic properties of the tissue. This invention is particularly, but not exclusively, useful in ophthalmic surgical procedures.

DISCUSSION OF THE PRIOR ART

It is well known that laser beams are useful to modify live tissue at the point where the beam is effectively focused onto the tissue. Further, it is known that laser beams can modify tissue in several ways depending on how the beam is constituted and focused. Specifically, under certain precisely controlled conditions, laser beams can create incisions in the tissue, decompose portions of the tissue, or cause the tissue to coagulate. As is to be expected, the specific effect a laser beam will have on a particular tissue is dependent on several variables.

While the particular tissue to be modified is not a variable, the physical characteristics of the tissue and the desired modification to be made on the tissue both significantly influence the characteristics of the laser beam which will be the most efficacious for the desired procedure. When discussing these beams, several important variables need to be considered. These are: (i) the wavelength of the light, (ii) the intensity of the beam, (iii) the size of the tissue area on which the beam is focused, and (iv) the length of time the beam is focused on the selected tissue. Presently used laser beams can be generally grouped into one of three categories. These categories are: continuous beams, pulsed beams, or what is commonly referred to as an Excimer laser.

A continuous laser beam is, as the name implies, a beam of substantially constant intensity whose duration lasts as long as the beam is turned on. Typically, this duration is on the order of one second or more. To somewhat off-set the adverse side effects such a relatively long duration may have on the tissue, a continuous beam typically has a low intensity which is on the order of one watt. Normally the wavelength of a continuous beam is selected from the visible range and is approximately 514 nanometers. Its major mechanical effect on tissue is thermal in nature. For modifying tissue, the continuous beam is focused onto an area which is approximately 50 microns in diameter. Because of its long duration, however, the thermal effects are not confined to the 50 micron diameter area. Instead, the thermal effect can, and generally does, adversely affect tissue within an area as large as 1 millimeter in diameter.

A pulsed laser beam, unlike the continuous beam, comprises bursts or pulses of light which are approximately 10 nanoseconds in duration. Typically, these pulses are separated by relatively long periods of quiescence. Due to these quescient periods, it is necessary for the intensity of each pulse to be relatively high, i.e. on the order of one megawatt. Normally the wavelength of light used for a pulsed laser beam is in the infrared range and will be approximately 1.06 microns or 10.6 microns. The primary mechanical effect on the tissue is acoustical, and although the beam is focused onto an area having a diameter of approximately 50 microns, this acoustic effect extends beyond the focused area to adversely affect tissue within an area as large as one millimeter in diameter.

Although the wavelengths of the Excimer laser are much shorter than those for the typical pulsed laser beam (the Excimer's wavelengths are in the ultraviolet range and have approximate values of 193 and 351 nanometers) its physical characteristics are very similar to the pulsed beam. The Excimer, however, is effectively an unfocused beam whose mechanical effect is both photochemical and acoustical. Due to its unfocused condition, the Excimer affects a relatively large area of tissue, i.e. an area approximately 1 millimeter in diameter. An example of a use for the Excimer laser in ophthalmic surgery is found in U.S. Pat. No. 4,665,913 which issued to L'Esperance Jr. for an invention entitled "Method for Ophthalmological Surgery." As disclosed and claimed in the '913 patent, the Excimer laser provides ultraviolet radiation to sculpt the anterior surface of the cornea. Importantly, the Excimer laser cannot be easily focused onto an area much less than one millimeter in diameter.

The obvious drawbacks of the above-described presently used laser beams stem primarily from the fact that for efficacious volumetric power density levels (i.e. beam intensity within a finite volume of tissue) their effect on tissue cannot be confined to relatively small volumes of tissue. Consequently, they have control problems and a propensity for causing unwanted trauma to peripheral tissue. The present invention has recognized that these difficulties can be effectively overcome by using a quasi-continuous beam. Specifically, the present invention recognizes that the effect of a quasi-continuous laser beam on tissue can be focused to a small spot size, confined to a small volume of tissue, and can be accurately controlled. Further, the present invention recognizes that the volumetric power density of a quasi-continuous laser beam can be varied to achieve different effects on tissue. For this purpose, it has been found that relatively high volumetric power densities will cause photoablation of tissue. On the other hand, relatively low volumetric power densities for the same beam can be used to change the visco-elastic properties of tissue. Both effects are efficaciously used for the present invention.

In general, a quasi-continuous laser beam according to the present invention is essentially a beam of monochromatic light which comprises an uninterrupted sequence of laser emissions having finite durations. A more complete and detailed discussion of the generation of a quasi-continuous laser beam is provided in our co-pending U.S. application Ser. No. 148,866 for an invention entitled "Multiwavelength Laser Source" which is assigned to the same assignee as the present invention. Additionally, wavelengths are used from both the visible and the infrared ranges. Preferably, the quasi-continuous laser beam will have a selectable wavelength of either 526 nanometers, 1.053 microns, or 2.94 microns. It will be understood, however, that these values are not absolute and are subject to some drift.

Apart from its wavelength and how the beam is actually generated, the physical characteristics of the generated quasi-continuous beam are of more than passing interest. Specifically, each emission in the quasi-continuous beam has an adjustable duration which is in the range of 1–40 picoseconds. Further, each emission has an intensity of approximately 10 megawatts and the repetition rate, or frequency of emissions, is on the order of ten thousand (10,000) emissions per second. Although the quiescent period between emissions is lengthy, relatively speaking, the result is an essentially uninterrupted sequence of emissions each having approximately 10 microjoules of energy. Importantly, in accordance with the delivery system disclosed in our co-pending U.S. application Ser. No. 151,569 for an invention entitled "3-Dimensional Laser Beam Guidance System" which is assigned to the same assignee as the present invention, the quasi-continuous laser beam can be focused onto an area of tissue which is only approximately 5–10 microns in diameter.

In accordance with the above, it is an object of the present invention to disclose a method for using a quasi-continuous laser beam which is efficacious in a variety of surgical procedures. It is another object of the present invention to disclose a method for using a laser beam having a variable volumetric power density which is efficacious for modifying tissue either by photoablation or by changing the visco-elastic properties of the tissue. Still another object of the present invention is to disclose a method for using a quasi-continuous laser beam which will efficaciously modify internal or superficial tissue. Yet another object of the present invention is to disclose the use of a laser beam which will minimize adverse effects on peripheral tissue. Another object of the present invention is to disclose a method for using a quasi-continuous laser beam in ophthalmic surgical procedures which is relatively easy to perform and which is cost effective.

SUMMARY OF THE INVENTION

The preferred method for using a quasi-continuous laser beam to change the optical properties of the eye or correct sight threatening diseases includes selecting both a wavelength and a volumetric power density for the beam which will accomplish the desired surgical procedure. The beam, which comprises an uninterrupted sequence of relatively very high intensity emissions having very short durations, is first focused at a start point in or on the tissue to be modified. The beam's focal point is then moved throughout a specified volume of the tissue, or along a specified path in the tissue, to modify the tissue on which the focal point is incident. According to the present invention, this movement of the beam's focal point is accomplished in a predetermined and controlled manner.

Depending on the selected volumetric power density setting for the laser beam, tissue can be modified by either photoablation of the tissue or by modifying the visco-elastic properties of the tissue. Further, depending on the specific volume affected by the beam or the specific path followed by the beam, a modification can be accomplished for either external tissue or internal tissue.

In accordance with the present invention, various surgical procedures can be performed to either change the optical properties of the eye or to cure sight threatening diseases of the eye. Specifically, the quasi-continuous laser beam of this invention can be used to make linear or curvilinear incisions into tissue to alter or remove tissue. Additionally, this beam can be used to drill holes or passageways through tissue and to coagulate tissue. Further, this beam can be used for photoablation of either superficial tissue or internal tissue. Still further, this beam can be used to modify the visco-elastic properties of internal tissue in a manner which softens the tissue. Accordingly, any surgical procedure requiring one or more of the above modifications to tissue can benefit from the use of the present invention.

Although the present invention is primarily concerned with ophthalmic surgical procedures, its applicability is very far reaching. The procedures of this invention will be efficacious for use in cardiovascular surgery, orthopedic surgery, hand surgery and neurosurgery; to name but a few. Further, although the use of optical fibers in the practice of the present invention is not herein disclosed in detail, it is to be understood that any optical system (including those with optical fibers) which will efficaciously deliver a quasi-continuous laser beam to a desired volume of tissue may be used.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 3 is a perspective view of an eye with portions broken away for clarity;

FIG. 4 is a cross-section of the cornea of the eye as seen along the line 4—4 in FIG. 3 in its relation to the lens of the eye;

DESCRIPTION OF THE PREFERRED METHOD

Figure 1:
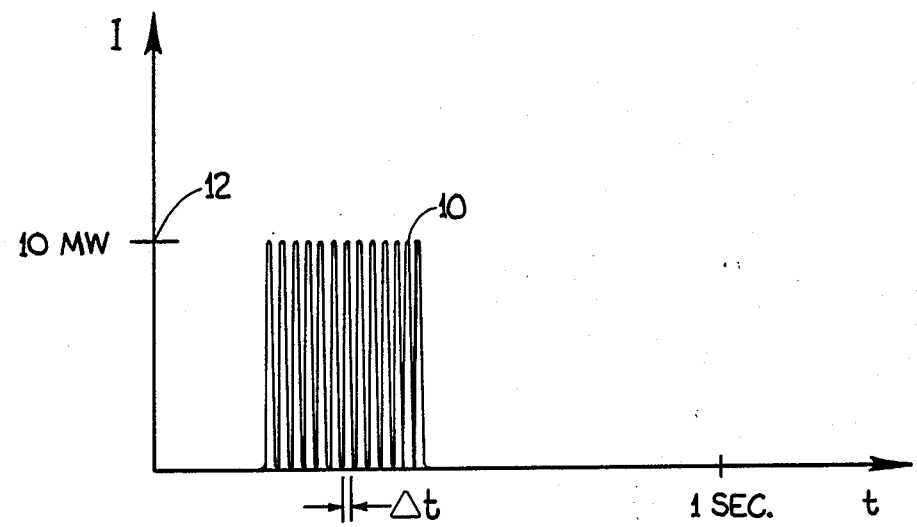
FIG. 1 is a plot of emission duration versus emission intensity for a plurality of emissions in the laser beam of the present invention.
Figure 1A:
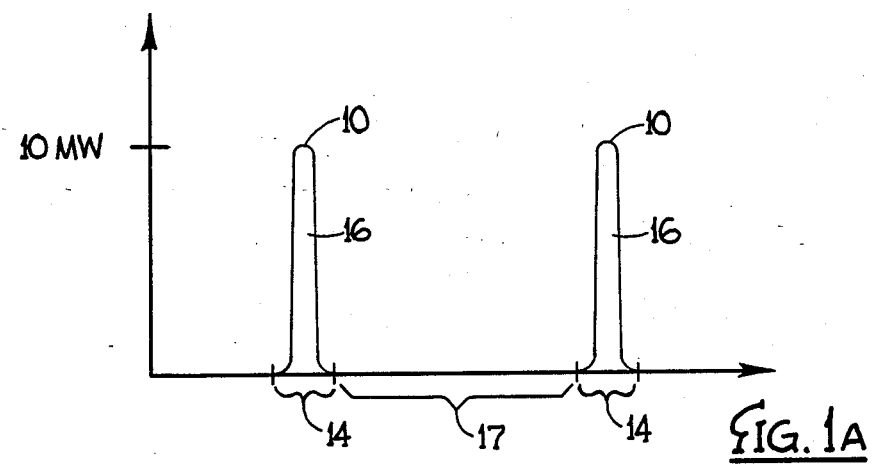
FIG. 1A is a plot of duration and intensity for a single emission over a finite time period.

The physical characteristics of a quasi-continuous laser beam for use in modifying tissue, as contemplated by the present invention, will be best understood by initially referring to both FIG. 1 and FIG. 1A. In FIG. 1, an uninterrupted sequence of emissions 10 is depicted in a plot of intensity (I) versus time (t). Though not shown to scale, in FIG. 1 each emission 10 is repeated at a rate of more than ten thousand (10,000) occurences per second. As shown in both FIG. 1 and FIG. 1A, each emission 10 has an intensity 12 which is approximately equal to ten (10) megawatts and each emission 10 lasts for a duration 14 which may be as short as approximately one (1) picosecond. The area 16 under the curve representing emission 10 equals the power in each emission 10 which, for the given parameters, will be approximately in a range that is less than ten (10) microjoules. Also, as shown in FIG. 1A, between each emission 10 there will be a quiescent period 17 which is substantially and significantly larger than duration 14. Nevertheless, due to the highly repetitive rate at which emissions 10 are generated, the practical result is a continuous and uninterrupted sequence of emissions 10 for the quasi-continuous beam. Importantly, each emission 10 can be focused down to an area of approximately five (5) microns in diameter.

In summary, a quasi-continuous laser beam as contemplated by the present invention comprises an effectively uninterrupted sequence of emissions 10. Each emission 10 has an intensity of approximately ten (10) megawatts and has a duration 14 of approximately one (1) picosecond. The emissions 10 are repeated at the rate of approximately ten thousand (10,000) repetitions per second, are focusable onto an area having an approximately five (5) micron diameter and can comprise wavelengths from the visible and infrared ranges which are efficacious for ophthalmic surgical procedures. As disclosed in our co-pending application for an invention entitled "Multiwavelength Laser Source," an active medium capable of generating multiple wavelengths for such a laser is YSGG:Cr:Nd:Er. More specifically, this active medium can generate laser beams having wavelengths of 526 nanometers, 1.053 microns and 2.94 microns.

Figure 2:
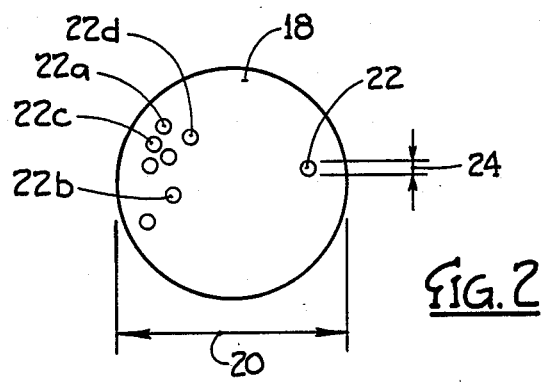
FIG. 2 is a schematic representation of an area of tissue to be modified.

FIG. 2 representatively shows one way in which a focused quasi-continuous beam can be used. In FIG. 2, a tissue area 18 having a diameter 20 of approximately fifty (50) microns is shown. As stated above, emissions 10 within the quasi-continuous laser beam can be focused onto a spot 22 having a diameter 24 which is as small as approximately five (5) microns. In accordance with subsequent disclosure, it will be seen that the spot size 22 can be varied. The volume of tissue to be affected by each emission 10, however, is essentially a constant for the quasi-continuous beam. This volume remains essentially constant at 1000 cubic microns. In order to efficaciously modify tissue within area 18, the quasi-continuous laser beam of the present invention will need to be focused at approximately one hundred (100) various locations throughout the area 18. The spots 22a, 22b, 22c and 22d represent a few of such locations within area 18 and the order of spots 22a, 22b, 22c and 22d is representative of only part of a firing sequence. Although the duration 14 of each emission 10 is very short and will have minimal effect on peripheral tissue, an apparently random firing order is established in order to insure the peripheral affects of the laser beam on tissue area 18 are, in fact, minimized.

In addition to an area or volume coverage for the quasi-continuous laser beam as discussed above with reference to FIG. 2, it will be appreciated that the various spots 22 can be rectilinearly or curvilinearly arranged and that the quasi-continuous beam can thereby be used as a means for making an incision into the tissue. Since each emission 10 will have only minimal, if any, effect on peripheral tissue, the emissions 10 can be focused in a side-by-side manner when linear incisions are to be made in the tissue.

As stated earlier, in addition to the frequency of emissions 10, the volumetric power density of each emission 10 in the quasi-continuous laser beam is of extreme importance. As used here, the term volumetric power density is not to be confused with what is referred to in some of the literature as irradiance. Unlike volumetric power density, irradiance contemplates an area rather than volume. With this in mind, volumetric power density is defined as the energy of an emission 10 for a specific duration 14 focused onto a given spot 22 which covers the volume of the tissue to be affected. Accordingly, power density can be varied by any of three mechanisms. First, the actual intensity or energy of the beam can be changed in accordance with the desires of the operator. Secondly, the spot 22 of tissue onto which the beam is focused can be altered. Thirdly, the duration 14 of each emission 10 can be varied. In either way, the volumetric power density of the beam can be effectively changed. Preferably, in order to maintain the benefits of a small focal size for a spot 22, the intensity of the beam is varied during internal ablation procedures to change the volumetric power density. On the other hand, for external ablation procedures it may be more efficacious to change the size of the focal spot 22. Normally, duration 14 is not changed.

As recognized by the present invention, the volumetric power density of a quasi-continuous beam can have a profound effect upon the manner in which the tissue is modified. For definitional purposes, volumetric power density is essentially photon energy/time/tissue volume. Accordingly, to analyze this term in light of the present invention, first consider photon energy. With a YSGG:Cr:Nd:Er crystal as used for the active medium of the present invention, three effective wavelengths can be generated. At the 2.94 micron wavelength generated by this active medium, the quasi-continuous beam comprises relatively small photons which each have approximately 0.4 eV of energy. On the other hand, the 1.053 micron wavelength light and the 526 nanometer wavelength light comprise increasingly larger photons having respectively 1.2 eV and 2.4 eV energy per photon. This is important, because regardless of the number of photons, a certain level of photon energy is required to break a tissue's molecular bonds.

Within tissue, a laser beam acts in two important ways to alter the tissue's molecular structure. The first way is by evaporation of water within the tissue and the other is by actually breaking certain of the bonds. Depending on the volumetric power density setting of the beam, this combination of water evaporation and bond breaking will either cause a total decomposition of the tissue's molecules by photoablation of intramolecular bonds or merely change the visco-elastic properties of the tissue by altering their intermolecular bonds. When only intermolecular bonds are broken, and only part of the water is evaporated, the tissue softens into a semi-liquified state.

The most important bonds which need to be broken in order to effectively modify living tissue are the C-N (Carbon-Nitrogen) bonds, the C-C (Carbon-Carbon) bonds and the H-C (Hydrogen-Carbon) bonds. Interestingly, each of these bonds requires the same approximate level of photon energy in order to break the bond. Specifically, the C-N bond requires 3.0 eV, the C-C bond requires 3.5 eV and the H-C bond requires 3.0 eV. In relation to the wavelengths which can be generated by the preferred active medium of the present invention, approximately two photons from the 526 nanometer wavelength laser beam are required to break one molecular bond, while four photons from the 1.053 micron wavelength laser beam or ten photons from the 2.94 microns wavelength laser beam are required to break the same molecular bond.

From the general definition of volumetric power density it is seen that time, i.e. the duration of each emission in the beam, is a significant factor. To discuss the importance of this factor, attention needs to again be given to the photons in the beam. More specifically, the consideration here centers on how many photons bombard the tissue within any given time period. It has been determined that, anatomically, the cornea of the eye is comprised of eighty percent (80%) water and twenty percent (20%) tissue. Therefore, approximately eighty percent (80%) of the photons in a given laser beam expend their energy evaporating water, while the remaining twenty percent (20%) expend their energies breaking molecular bonds. To be effective for these purposes, however, the photons must react with the tissue molecules at substantially the same point in time. Their efficacy is significantly diminished as the time period is extended. For the present invention, the duration of each emission 10 is within an efficacious time period which is measured in picoseconds.

As the term itself implies, volumetric power density is concerned with volume. Interestingly, with the quasi-continuous laser beam, the photon energy and emission duration are varied such that a substantially constant volume of tissue will be modified regardless of the size of the area onto which the beam is focused. It happens that the affected volume of tissue is approximately one thousand cubic microns (1000 um$^3$). Accordingly, the depth to which the emission 10 will penetrate into the tissue is dependent on the area of spot 22 onto which emission 10 is focused. Practically, this depth can vary between 0.2 microns and approximately 10 microns.

In light of the above, the process of tissue modification can be generally discussed. Recognize that during this process, both bond breaking and water evaporation in the tissue occur simultaneously, though not necessarily proportionally. Also, recognize that between a zero volumetric power density and a volumetric power density where there is complete photoablation of the tissue, there is an intermediate transition range in which the resultant tissue modification is something less than complete photoablation. Specifically, at very low levels of volumetric power density, there will be no modification of tissue. As the volumetric power density is increased, however, water begins to evaporate. In this regime where mostly water is evaporated and relatively few molecular bonds are being broken, the tissue is modified and softened into a semi-liquid state. This process continues as volumetric power density is increased until holes eventually begin to appear in the tissue. At a volumetric power density level equal to approximately four (4) microjoules/picosecond/1000 cubic microns, complete photoablation starts to occur. At this point, all water is evaporated and all bonds are effectively broken. It should be noted that the four (4) microjoule/picosecond/1000 cubic microns demarcation is not absolute. Indeed, the transitional power setting will depend, in part, on the hardness of the tissue to be modified. Five (5) or six (6) microjoules/picosecond/1000 cubic microns may be required before photoablation will occur. Also, it may be that 5-6 microjoules/picosecond/1000 cubic microns are required before the visco-elastic properties of the tissue are effectively modified.

The actual number of microsurgical procedures which can be performed using a quasi-continuous laser beam is effectively limited only by the skill and ingenuity of the operator. Accordingly, the following described procedures are only exemplary and are not intended to be all inclusive or limiting. Further, although the emphasis here is placed on ophthalmic surgical procedures, it is to be understood that the quasi-continuous beam will be efficacious for procedures on other living tissue in addition to eye tissue.

As a general proposition, the quasi-continuous laser beam of the present invention can be used in refractive surgery, filtration surgery, laserphakoemulsification, capsulotomies and retinal surgery. Within each of these general areas, several specific procedures can be discussed to illustrate, in detail, the broad range of potential applications.

In refractive surgery, it is well known that myopia, hyperopia and astigmatism can be corrected either by reshaping the cornea or by reconstituting the cornea with corneal transplants. In either case, corneal tissue must be modified or removed in some manner. According to the present invention, this can be done in any of several ways. Specifically, the methods of the present invention contemplate refractive correction of the above-identified optical difficulties by either internal or external modification of eye tissue through either photoablation or changing the visco-elastic properties of the tissue.

First, consider those refractive surgical procedures for reshaping the eye which are accomplished by making incisions into the cornea. FIG. 3 is a perspective view of an eye 26 with part of its cornea 28 broken away for clarity. FIG. 3 shows an incision 30 which has been made into cornea 28. The incision 30 can be perhaps best appreciated by cross-referencing FIG. 3 with FIG. 4 wherein a cross-sectional view of incision 30 shows that such an incision 30 typically penetrates the epithelium 32, Bowman's membrane 34 and into the stroma 36 of cornea 28. For apparent reasons, care must be taken to not penetrate Descemet's membrane 38 or the endothelium 40 with an incision 30. In accordance with the present invention, incision 30 is made into the cornea by establishing a start point for incision 30 on cornea 28 and then tracing the quasi-continuous laser beam back and forth along the line of incision 30 until the desired depth into the stroma 36 has been achieved.

As implied above, incision 30 is made by a photoablation process in which a train of emissions 10 each separately impact the exposed tissue along a linear path. Preferably, the wavelength selected for this procedure will be either 526 nanometers, 1.053 microns or 2.94 microns and the volumetric power density setting will be greater than four (4) microjoules/picosecond/1000 cubic microns.

Incisions 30 are made into cornea 28 depending on the desired result in reshaping cornea 28. For example, incisions 30 can be made according to well known radial keratotomy procedures for correcting myopia or astigmatism. Similarly, incisions 30 can be made according to well known procedures for making T-cuts to correct astigmatism. In each case the object is to weaken cornea 28 along predetermined lines on cornea 28 so that fluid pressure from the aqueous humor 42 inside eye 26 will cause cornea 28 to be reshaped and optically corrected.

It is also well known that the optical properties of eye 26 can be corrected by removing a portion of cornea 28. The portion 44 shown in FIGS. 3 and 4 is only exemplary of a removed portion and is not intended in any way to represent a desired procedure. Indeed, the actual shape and dimensions for a removed portion 44 will depend entirely on the desires of the operator in accordance with well known procedures to prevent or correct a diagnosed optical problem.

One way in which removal of a portion 44 from the cornea 28 can be accomplished in accordance with the present invention is by directing the quasi-continuous beam onto a defined surface area of the cornea 28. This area is then bombarded with emissions 10 for the modification of a tissue area 18 as described above in connection with the description of FIG. 2 for modification of tissue area 18. It will be appreciated that within each tissue area 18, each emission 10 will preferably affect tissue to a depth of approximately 0.4 microns. Thus, portion 44 can be defined by a finite number of tissue areas 18 which are each 1 millimeter in diameter and 0.4 microns deep. Importantly, spots 22 are moved within the volume of tissue defined by portion 44 in a programmed manner so that all tissue within portion 44 is eventually affected. Also importantly, this movement of spots 22 is accomplished in a sequence which prevents an excessive accumulation of laser energy within any part of the tissue. The volumetric power density setting for this procedure is preferably above four (4) microjoules/picosecond/1000 cubic meters and the wavelength of the beam is selected from those including 526 nanometers, 1.053 microns or 2.94 microns. Additionally, focal spot 22 should be preferably between 5 and 10 microns in diameter for 526 nanometers and 1.053 micron wavelength and between 35 and 70 microns in diameter at the 2.94 micron wavelength.

Interestingly, the process of creating external ablations with emissions 10 of a quasi-continuous laser beam has a particular advantage over present technology insofar as intensity efficiency is concerned. Specifically, because emissions 10 have such a short duration, any interaction they might have had with debris that is dispelled from the tissue during photoablation is effectively avoided. It is known that during photoablation, vaporized tissue material is expelled from the tissue site. It is also known that this debris can scatter photons in the incoming laser beam. As should be expected, this reduces the irradiance of the beam. The shorter duration emissions in the quasi-continuous beam, however, allow them to modify the tissue before the debris is ejected from the site. Thus, they effectively avoid the dispelled debris from the photoablative process. Additionally, it has been determined that a laser's effect occurs within a period of ten (10) picoseconds. This, of course, is the approximate duration of each emission 10 of the quasi-continuous beam. Accordingly, substantially all of the energy in emissions 10 of the quasi-continuous beam is available for the photoablative process. It follows that the longer pulses of other presently used lasers are not so efficient.

Another effect which occurs during photoablation which is effectively diminished by the quasi-continuous beam is tissue recoil. This occurs when tissue evaporates as it is being modified by photoablation. Typically, this evaporation is explosive in nature and causes a vibratory or acoustic effect within the tissue. The magnitude of this effect, which can cause trauma to tissue, is proportional to the beam's energy level, i.e. the number of photons which are present in the laser beam. By limiting the number of photons in the emissions 10 of the beam, as happens with the quais-continuous beam of this invention, the recoil process in the tissue and the consequent acoustic effect is significantly diminished.

Returning now to FIG. 4, it is to be understood that the removed portion 44 may be sculpted from the cornea 28 as disclosed above to provide the corrective optical properties desired. On the other hand, removed portion 44 may be taken away to prepare a site into which a corneal transplant can be placed. Such a site is not necessarily limited to the external surface of cornea 28. As shown in FIG. 4, an internal portion 46 might also be removed from cornea 28 for purposes of preparing a site into which an implant can be placed.

As will be appreciated by the skilled artesan, portion 44 and portion 46 can be removed from cornea 28 in either of two ways. First, entire portion 44 or portion 46 can be decomposed by photoablation. Portion 44 or 46 may also, however, be excised from cornea 28 by cutting a path therearound. For example, as shown in FIG. 4, portion 46 is severed from cornea 28 by cutting cornea 28 along path 47.

In the particular case where an external portion 44 is removed from cornea 28 the result is an exposed surface 48. It has been found that such a surface 48 is left with craters 50 which cause irregularities in the surface 48. For example, the Excimer laser leaves irregularities which present depth variations in surface 48 that are on the order of 0.5 microns. Although epithelial elements may eventually cover surface 48, craters 50 having irregularities on the order of 0.5 microns will remain. It has been determined that craters 50 of this size cause hazy vision for a patient.

Again, the quasi-continuous beam has an advantage. It happens that surface irregularities caused by the quasi-continuous beam of the present invention are of significantly diminished dimensions. More specifically, because each emission 10 can be focused onto a spot 22 having a depth of 0.2 microns, craters 50 on surface 48 of a removed portion 44 typically are on the order of only 0.2 microns. Irregularities of this magnitude are not so optically significant. Thus, a quasi-continuous beam can effectively "polish" the superficial tissue.

Figure 5:
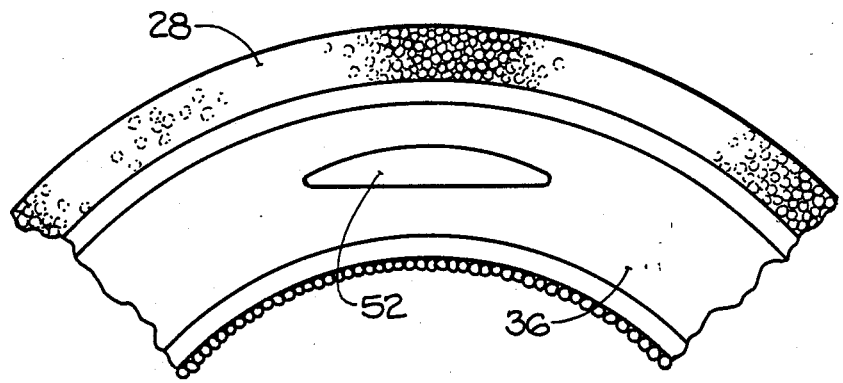
FIG. 5 is a cross-section of the eye substantially as seen in FIG. 4 showing an internal tissue modification.
Figure 6:
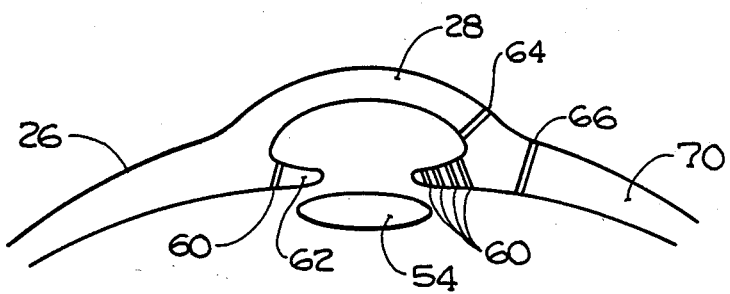
FIG. 6 is a schematic diagram of a cross-section of the eye showing the relationship between the cornea and the lens.

As implied above, the quasi-continuous beam of the present invention is also effective for internal ablation, i.e. the ablation of tissue which is wholly nonsuperficial and unexposed. As an example, FIG. 5 shows a region 52 in stroma 36 which is representative of an internal ablation. In accordance with the present invention, region 52 could be located anywhere within stroma 36 according to the desires of the operating physician. More specifically, region 52, or a plurality of regions 52, can be located within stroma 36 of cornea 28 at effective locations for performing a radial keratotomy or making T-cuts to correct myopia, hyperopia or astigmatism. Additionally, tissue within region 52 can be either decomposed by photoablation to cause cavitation or modified into a semi-liquified state by changing the viscoelastic properties of the tissue. For either procedure the quasi-continuous beam preferably includes wavelengths of 526 nanometers or 1.053 microns or 2.94 microns. If cavitation is to be effected, the volumetric power density of the beam should be above the four (4) microjoule/picosecond/1000 cubic micron level. Tissue within the region 52 is modified either by scanning the focal spot of the quasi-continuous beam throughout the region or by selecting volumes within region 52 for selective ablation.

As stated above, both capsulotomy and laserphako-emulsification operations on the lens 54 of an eye 26 are possible with the quasi-continuous beam of the present invention. More specifically, for cataract surgery a region 56 of lens 54 may be modified to effect the optical properties of the lens 54. For example, in a posterior capsulotomy, it is typical that a region 56 of lens 54 be removed and an implant be inserted therefor. This can be done by using the quasi-continuous beam to cut region 56 from lens 54. In a different procedure involving lens 54, the interior tissue of lens 54 may be either evaporated by photoablation for cavitation of the region 56 or modified to cause its semi-liquification. The object in either case is to prevent presbyopia. As with the other surgical procedures discussed here, the wavelengths preferably used for the capsulotomy and laserphakoemulsification operations are selected from wavelengths of 526 nanometers, 1.053 microns or 2.94 microns.

Filtration surgery is another surgical area in which the quasi-continuous beam can be useful. In general, the various filtration surgical procedures require penetration of tissue to create a channel through which fluid can flow to relieve fluid pressure build-up within the eye 26. In effect, through the process of photoablation, a passageway needs to be drilled through the tissue. For such a procedure, the beam needs to be focused at a start point on the surface of the tissue and subsequently moved along a path which will accomplish the desired photoablation. It is preferable that the selected wavelength for the quasi-continuous laser beam to be used in the procedure be approximately 526 nanometers, 1.053 microns or 2.94 microns. Additionally, volumetric power density levels, i.e. those above four (4) microjoules/picosecond/1000 cubic microns, which are sufficient to cause photoablation, will be required. Examples of filtration surgery include an iridectomy.

For such a procedure, a passageway 60 can be created through iris 62. Further, it will be understood that a plurality of passageways 60 can be made through iris 62 by this procedure. Regardless whether a single passageway 60 is created or a plurality of passageways 60 are created, the objective in either case is to allow fluid from within the aqueous humor 42 of eye 26 to flow into the area between cornea 28 and lens 54 to relieve fluid pressure build-up within eye 26. In another filtration surgery procedure, it is necessary that a channel 64 be drilled through the cornea 28 to open Schlemm's canal. This is a procedure well known in the pertinent art and one which can be accomplished by use of the quasi-continuous beam of the present invention using the wavelengths and volumetric power density levels set forth above for the iridectomy. Still another filtration surgery procedure which can be accomplished under the present invention is a sclerotomy. In this procedure a passageway 66 is provided through sclera 70 into the anterior chamber of the eye 26 to allow for relief of glaucoma.

Figure 7:
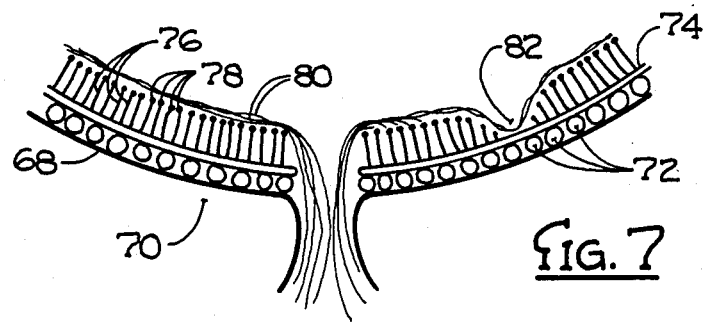
FIG. 7 is a schematic drawing of a cross-section of the retina of the eye.

Retinal surgery is still another area in which a quasi-continuous laser beams can be effective. In particular, the procedure for preventing macular degeneration is of interest. Unlike work on the cornea, work on the retina involves several different tissues which each react differently to laser energy. This will be best appreciated by reference to FIG. 7 wherein the retina 68 of an eye is shown. Briefly, as shown in FIG. 7, retina 68 is based on the sclera 70. Interior to sclera 70 are many blood vessels which comprise the choroid 72 and on top of choroid 72 is a layer of retinal pigment epithelium 74. Receptors 76 which comprise the more familiar rods and cones of retina 68 are on the retinal pigment epithelium 74 and separate it from nuclei 78 and ganglion cells 80. Insofar as macular degeneration is concerned, the area of retina 68 in the region of fovea 82 is of particular importance. As is well known to the skilled artisan, the fovea 82 is a depression in retina 68 where detachments and related problems are most likely to occur.

Specifically, when working with tissue such as the fovea 82, there is tissue such as retinal pigment epithelium 74 which absorbs light around 526 nanometers. Therefore, this wavelength is ineffective. Also, it is known that cornea 28 will absorb light around the 2.94 micron wavelength. Therefore, light at the 2.94 wavelength does not effectively arrive at retina 68. Thus it is necessary to use the 1.053 micron wavelength for retinal surgery. Volumetric power density settings for these procedures, like those for all other procedures herein described, will depend on the desired modification of the tissue. Very specifically, it may be necessary to lower the volumetric power density to levels that are effective for coagulating blood vessels in the choroid 72.

While the methods as herein disclosed in detail are fully capable of obtaining the objects and providing the advantages herein before stated, it is to be understood that they are merely illustrative of the presently preferred methods according to the present invention and that no limitations are intended to the details of construction or design herein shown other than as described in the appended claims.

We claim:

1. A method for modifying tissue with a quasi-continuous laser beam comprising an uninterrupted sequence of emissions each having a finite duration which comprises:

generating a beam of laser pulses, said beam comprising an uninterrupted sequence of at least one thousand pulses lasting for at least one second, wherein each of said pulses has less than 30 microjoules (30 uj) energy and is approximately one picosecond (1 psec) in duration;

establishing a start point in said tissue;

focusing said laser beam onto said start point;

selecting a volumetric power density for said laser beam; and scanning said beam along a predetermined path in said tissue to modify said tissue along said path.

2. A method for modifying tissue with a quasi-continuous laser beam as recited in claim 1 wherein selecting said volumetric power density is accomplished by varying the size of said spot whereon said laser beam is focused.

3. A method for modifying tissue with a quasi-continuous laser beam as recited in claim 1 wherein selecting said volumetric power density is accomplished by varying the duration of said emissions.

4. A method for modifying tissue with a quasi-continuous laser beam as recited in claim 1 wherein selecting said volumetric power density is accomplished by varying the energy of said emissions.

5. A method for modifying tissue with a quasi-continuous laser beam as recited in claim 1 further comprising the step of choosing a wavelength for said laser beam.

6. A method for modifying tissue with a quasi-continuous laser beam as recited in claim 5 wherein said wavelength is greater than 400 nanometers.

7. A method for modifying tissue with a quasi-continuous laser beam as recited in claim 5 further comprising the step of fixing a reference datum relative to said tissue, and said moving of said focal spot from said start point is done relative to said reference datum.

8. A method for modifying tissue with a quasi-continuous laser beam as recited in claim 5 wherein said selecting step generates a quasi-continuous laser beam having a volumetric power density which changes the visco-elastic properties of the tissue to create a semi-liquification of said tissue at said focal spot of said beam.

9. A method for modifying tissue with a quasi-continuous laser beam as recited in claim 5 wherein said selecting step generates a quasi-continuous laser beam having a volumetric power density which modifies the tissue by photoablation at said focal spot of said beam.

10. A method for modifying tissue with a quasi-continuous laser beam as recited in claim 9 wherein said selected volumetric power density is characterized by emissions in said quasi-continuous laser beam having more than 4 microjoules of energy and a duration less than 10 picoseconds focused on an area of said tissue having less than a 10 micron diameter.

11. A method for modifying tissue with a quasi-continuous laser beam as recited in claim 10 wherein movement of said focal spot is confined to the interior of a selected tissue.

12. A method for modifying tissue with a quasi-continuous laser beam as recited in claim 10 wherein moving said focal spot penetrates said tissue to create a passageway therethrough.

13. A method for modifying tissue with a quasi-continuous laser beam as recited in claim 10 wherein said chosen wavelength is approximately 526 nanometers or approximately 1.053 microns or approximately 2.94 microns and said beam is focused on the cornea of an eye to make T-cut incisions or incisions for a radial keratotomy.

14. A method for modifying tissue with a quasi-continuous laser beam as recited in claim 10 wherein said chosen wavelength is approximately 526 nanometers or approximately 1.053 microns or approximately 2.94 microns and said beam is focused onto the cornea of an eye for causing modification thereof to correct myopia, hyperopia or astigmatism.

15. A method of using a quasi-continuous laser beam for changing the optical properties of the eye which comprises the steps of:
generating a beam of laser pulses, said beam comprising an uninterrupted sequence of at least one thousand pulses lasting for at least one second, wherein each of said pulses has less than 30 microjoules (30 uj) energy and is approximately one picosecond (1 psec) in duration;
Identifying a reference datum on the eye;
Focusing said laser beam at a selected point relative to said datum;
Selecting a volumetric power density for said quasi-continuous laser beam; and
Scanning the focal point relative to said datum in accordance with a predetermined movement to alter tissue at the focal point.

16. A method of using a quasi-continuous laser beam for changing the optical properties of the eye as recited in claim 15 wherein selecting said volumetric power density is accomplished by varying the size of said spot whereon said laser beam is focused.

17. A method of using a quasi-continuous laser beam for changing the optical properties of the eye as recited in claim 15 wherein said quasi-continuous beam comprises an uninterrupted sequence of laser emissions having finite durations and selecting said volumetric power density is accomplished by varying the duration of said emissions.

18. A method of using a quasi-continuous laser beam for changing the optical properties of the eye as recited in claim 15 wherein said reference datum is a surface of said tissue.

19. A method of using a quasi-continuous laser beam for changing the optical properties of the eye as recited in claim 18 wherein said reference datum further comprises the optical axis of said eye.

20. A method of using a quasi-continuous laser beam for changing the optical properties of the eye as recited in claim 15 further comprising the step of choosing a wavelength for said laser beam.

21. A method of using a quasi-continuous laser beam for changing the optical properties of the eye as recited in claim 20 wherein said chosen wavelength is greater than substantially 400 nanometers.

22. A method of using a quasi-continuous laser beam for changing the optical properties of the eye as recited in claim 21 wherein said selecting step generates a quasi-continuous laser beam having a volumetric power density which changes the visco-elastic properties of the tissue to create a semiliquification of said tissue at said focal spot of said beam.

23. A method of using a quasi-continuous laser beam for changing the optical properties of the eye as recited in claim 22 wherein said selected volumetric power density is characterized by emissions in said quasi-continuous laser beam having less than 4 microjoules of energy and a duration less than 10 picoseconds focused on an area of said tissue having less than a 10 micron diameter.

24. A method of using a quasi-continuous laser beam for changing the optical properties of the eye as recited in claim 22 wherein movement of said focal spot is confined to the interior of a selected tissue.

25. A method of using a quasi-continuous laser beam for changing the optical properties of the eye as recited in claim 24 wherein said chosen wavelength is approximately 526 nanometers or approximately 1.053 microns and said beam is focused into the cornea of an eye for causing an internal modification thereof to correct myopia, hyperopia or astigmatism.

26. A method of using a quasi-continuous laser beam for changing the optical properties of the eye as recited in claim 24 wherein said beam is focused into the lens of an eye for causing an internal modification thereof to prevent presbyopia.

27. A method of using a quasi-continuous laser beam for changing the optical properties of the eye as recited in claim 21 wherein said selecting step generates a quasi-continuous laser beam having a volumetric power density which modifies the tissue by photoablation at said focal spot of said beam.

28. A method of using a quasi-continuous laser beam for changing the optical properties of the eye as recited in claim 27 wherein said selected volumetric power density is characterized by emissions in said quasi-continuous laser beam having more than 4 microjoules of energy and a duration less than 10 picoseconds focused on a volume of said tissue of less than 1000 cubic microns.

29. A method of using a quasi-continuous laser beam for changing the optical properties of the eye as recited in claim 27 wherein movement of said focal spot is confined to the interior of a selected tissue.

30. A method of using a quasi-continuous laser beam for changing the optical properties of the eye as recited in claim 29 wherein said chosen wavelength is approximately 526 nanometers or approximately 1.053 microns and said beam is focused into the cornea of an eye for causing an internal modification thereof to correct myopia, hyperopia or astigmatism.

31. A method of using a quasi-continuous laser beam for changing the optical properties of the eye as recited in claim 29 wherein said beam is focused into the lens of an eye for causing an internal modification thereof to prevent presbyopia.

32. A method of using a quasi-continuous laser beam for changing the optical properties of the eye as recited in claim 27 wherein movement of said focal spot is confined to a volume of tissue, a portion of which defines part of the surface of said tissue.

33. A method of using a quasi-continuous laser beam for changing the optical properties of the eye as recited in claim 32 wherein said chosen wavelength is approximately 526 nanometers, 1.053 microns or approximately 2.94 microns and said beam is focused onto the cornea of an eye for causing a modification thereof to correct myopia, hyperopia or astigmatism.

34. A method of using a quasi-continuous laser beam for changing the optical properties of the eye as recited in claim 32 wherein said chosen wavelength is approximately 526 nanometers or approximately 1.053 microns or approximately 2.94 microns and said beam is focused on the cornea of an eye to make T-cut incisions or incisions for a radial keratotomy.

35. A method of using a quasi-continuous laser beam for changing the optical properties of the eye as recited in claim 27 wherein moving said focal spot penetrates said tissue to create a passageway therethrough.

36. A method of using a quasi-continuous laser beam for changing the optical properties of the eye as recited in claim 61 wherein said chosen wavelength is approximately 526 nanometers or approximately 1.053 microns and said beam is focused onto the iris of an eye for performing an iridectomy.

37. A method of using a quasi-continuous laser beam for changing the optical properties of the eye as recited in claim 35 wherein said chosen wavelength is approximately 526 nanometers or approximately 1.053 microns and said beam is focused onto the iris of an eye for creating a plurality of said passageways therethrough.

38. A method of using a quasi-continuous laser beam for changing the optical properties of the eye as recited in claim 35 wherein said chosen wavelength is approximately 526 nanometers or approximately 1.053 microns and said beam is focused onto the sclera of an eye for performing a sclerotomy.

39. A method of using a quasi-continuous laser beam for changing the optical properties of the eye as recited in claim 35 wherein said chosen wavelength is approximately 526 nanometers or approximately 1.053 microns or approximately 2.94 microns and said beam is focused onto the cornea of an eye for opening Schlemm's canal.

40. A method for correcting optical deficiencies of the eye by using a quasi-continuous laser beam to reshape the anterior surface of the cornea or make incisions into the anterior surface to the cornea which comprises the steps of:
generating a beam of laser pulses, said beam comprising an uninterrupted sequence of at least one thousand pulses lasting for at least one second, wherein each of said pulses has less than 30 microjoules (30 uj) energy and is approximately one picosecond (1 psec) in duration;
establishing a start point on the cornea of the eye;
choosing a wavelength for said laser beam which is greater than 400 nanometers;
focusing said laser beam onto a spot which covers said start point;
selecting a volumetric power density for said laser beam which is sufficiently greater than 4 microjoules/picosecond/1000 cubic microns to cause photoablation of the tissue;
defining the tissue to be modified by said laser beam; and
moving the focal spot of said laser beam from the start point through the tissue to be modified.

41. A method for correcting optical deficiencies of the eye by using a quasi-continuous laser beam to create a cavity within the stroma of the cornea of an eye or to modify tissue within the stroma of the cornea of an eye by changing its visco-elastic properties which comprises the steps of:
generating a beam of laser pulses, said beam comprising an uninterrupted sequence of at least one thousand pulses lasting for at least one second, wherein each of said pulses has less than 30 microjoules (30 uj) energy and is approximately one picosecond (1 psec) in duration;
establishing a start point within the stroma;
choosing a wavelength for said laser beam which is greater than 400 nanometers;
focusing said laser beam onto a spot which covers said start point;
selecting a volumetric power density for said laser beam;
defining the volume of tissue to be modified by said laser beam; and
moving the focal spot of said laser beam from said start point within said volume of tissue to other predetermined spots in said volume of tissue to modify said tissue according to said selected volumetric power density.

42. A method for relieving glaucoma by using a quasi-continuous laser beam to open fluid passageways through tissue which comprises the steps of:
generating a beam of laser pulses, said beam comprising an uninterrupted sequence of at least one thousand pulses lasting for at least one second, wherein each of said pulses has less than 30 microjoules (30 uj) energy and is approximately one picosecond (1 psec) in duration;
establishing a start point in said tissue;
choosing a wavelength for said beam which is greater than 400 nanometers;
focusing said laser beam onto a spot which covers said start point;
selecting a volumetric power density for said laser beam which is sufficiently greater than 4 microjoules/picosecond/1000 cubic microns to cause photoablation of the tissue;
defining the tissue to be modified by said laser beam; and
moving the focal spot of said laser beam from the start point through the tissue to be modified.

43. A method for correcting optical deficiencies of the eye by using a quasi-continuous laser beam to remove cataracts from the lens of the eye, to perform a capsulectomy or to modify the interior tissue of the lens by changing the vico-elastic properties of the lens tissue which comprises the steps of:
generating a beam of laser pulses, said beam comprising an uninterrupted sequence of at least one thousand pulses lasting for at least one second, wherein each of said pulses has less than 30 microjoules (30 uj) energy and is approximately one picosecond (1 psec) in duration;
establishing a start point on said lens;

focusing said laser beam onto a spot which covers said start point;

choosing a wavelength for said beam which is in the visual or infrared range and above 400 nanometers;

selecting a volumetric power density for said laser beam;

defining a volume of said tissue to be modified by said laser beam; and moving the focal spot of said laser beam from said start point within said volume of tissue to affect said tissue according to said selected volumetric power density.

44. A method for the treatment of macular degeneration on the retina of the eye using a quasi-continuous laser beam which comprises the steps of:

generating a beam of laser pulses, said beam comprising an uninterrupted sequence of at least one thousand pulses lasting for at least one second, wherein each of said pulses has less than 30 microjoules (30 uj) energy and is approximately one picosecond (1 psec) in duration;

establishing a start point on said retina;

focusing said laser beam onto a spot which covers said start point;

choosing a wavelength for said beam of approximately 1.053 microns;

selecting a volumetric power density for said laser beam;

defining the area of tissue to be modified by said laser beam; and moving the focal spot of said laser beam from said start point within said volume of tissue to modify said tissue according to said selected volumetric power density.

45. A method for modifying tissue with a quasi-continuous laser beam which comprises:

generating a beam of laser pulses, said beam comprising an uninterrupted sequence of at least one thousand pulses lasting for at least one second, wherein each of said pulses has less than 30 microjoules (30 uj) energy and is approximately one picosecond (1 psec) in duration;

establishing a start point in said tissue;

focusing said laser beam onto a spot which covers said start point;

selecting a volumetric power density for said laser beam;

defining a volume of tissue to be modified by said laser beam; and moving the focal spot of said laser beam from said start point within said volume of tissue to other predetermined spots in said volume of tissue to modify said tissue according to said selected volumetric power density.

46. A method for modifying tissue with a quasi-continuous laser beam as recited in claim 45 wherein selecting said volumetric power density is accomplished by varying the size of said spot whereon said laser beam is focused.

47. A method for modifying tissue with a quasi-continuous laser beam as recited in claim 45 wherein said quasi-continuous beam comprises an uninterrupted sequence of laser emissions having finite durations and selecting said volumetric power density is accomplished by varying the duration of said emissions.

48. A method for modifying tissue with a quasi-continuous laser beam as recited in claim 45 wherein said quasi-continuous beam comprises an uninterrupted sequence of laser emissions having finite durations and selecting said volumetric power density is accomplished by varying the energy of said emissions.

49. A method for modifying tissue with a quasi-continuous laser beam as recited in claim 45 further comprising the step of choosing a wavelength for said laser beam.

50. A method for modifying tissue with a quasi-continuous laser beam as recited in claim 44 wherein said wavelength is greater than 400 nanometers.

51. A method for modifying tissue with a quasi-continuous laser beam as recited in claim 49 further comprising the step of fixing a reference datum relative to said tissue, and said moving of said focal spot from said start point is done relative to said reference datum.

52. A method for modifying tissue with a quasi-continuous laser beam as recited in claim 49 wherein said selecting step generates a quasi-continuous laser beam having a volumetric power density which changes the visco-elastic properties of the tissue to create a semi-liquification of said tissue at said focal spot of said beam.

53. A method for modifying tissue with a quasi-continuous laser beam as recited in claim 52 wherein movement of said focal spot is confined to the interior of a selected tissue.

54. A method for modifying tissue with a quasi-continuous laser beam as recited in claim 53 wherein said chosen wavelength is approximately 526 nanometers or approximately 1.053 microns and said beam is focused into the cornea of an eye for causing an internal modification thereof to correct myopia, hyperopia or astigmatism.

55. A method for modifying tissue with a quasi-continuous laser beam as recited in claim 53 wherein said beam is focused into the lens of an eye for causing an internal modification thereof to prevent presbyopia.

56. A method for modifying tissue with a quasi-continuous laser beam as recited in claim 52 wherein said selected volumetric power density is characterized by emissions in said quasi-continuous laser beam having less than 4 microjoules of energy and a duration less than 10 picoseconds focused on an area of said tissue having less than a 10 micron diameter.

57. A method for modifying tissue with a quasi-continuous laser beam as recited in claim 49 wherein said selecting step generates a quasi-continuous laser beam having a volumetric power density which modifies the tissue by photoablation at said focal spot of said beam.

58. A method for modifying tissue with a quasi-continuous laser beam as recited in claim 57 wherein said selected volumetric power density is characterized by emissions in said quasi-continuous laser beam having more than 4 microjoules of energy and a duration less than 10 picoseconds focused on a volume of said tissue of approximately 1000 cubic microns.

59. A method for modifying tissue with a quasi-continuous laser beam as recited in claim 57 wherein movement of said focal spot is confined to the interior of a selected tissue.

60. A method for modifying tissue with a quasi-continuous laser beam as recited in claim 59 wherein said chosen wavelength is approximately 526 nanometers or approximately 1.053 microns and said beam is focused into the cornea of an eye for causing an internal modification thereof to correct myopia, hyperopia or astigmatism.

61. A method for modifying tissue with a quasi-continuous laser beam as recited in claim 14 wherein said beam is focused into the lens of an eye for causing an internal modification thereof to prevent presbyopia.

62. A method for modifying tissue with a quasi-continuous laser beam as recited in claim 57 wherein movement of said focal spot is confined to a volume of tissue, a portion of which defines part of the surface of said tissue.

63. A method for modifying tissue with a quasi-continuous laser beam as recited in claim 62 wherein said chosen wavelength is approximately 2.94 microns and said beam is focused onto the cornea of an eye for causing a modification thereof to correct myopia, hyperopia or astigmatism.

64. A method for modifying tissue with a quasi-continuous laser beam as recited in claim 62 wherein said chosen wavelength is approximately 526 nanometers or approximately 1.053 microns and said beam is focused onto the retina of an eye for preventing or correcting macular degeneration.

65. A method for modifying tissue with a quasi-continuous laser beam as recited in claim 57 wherein moving said focal spot penetrates said tissue to create a passageway therethrough.

66. A method for modifying tissue with a quasi-continuous laser beam as recited in claim 65 wherein said chosen wavelength is approximately 526 nanometers or approximately 1.053 microns and said beam is focused onto the iris of an eye for performing an iridectomy.

67. A method for modifying tissue with a quasi-continuous laser beam as recited in claim 65 wherein said chosen wavelength is approximately 526 nanometers or approximately 1.053 microns and said beam is focused onto the iris of an eye for creating a plurality of said passageways therethrough.

68. A method for modifying tissue with a quasi-continuous laser beam as recited in claim 65 wherein said chosen wavelength is approximately 526 nanometers or approximately 1.053 microns or approximately 2.94 microns and said beam is focused onto the sclera of an eye for performing a sclerotomy.

69. A method for modifying tissue with a quasi-continuous laser beam as recited in claim 65 wherein said chosen wavelength is approximately 526 nanometers or approximately 1.053 microns or approximately 2.94 microns and said beam is focused onto the cornea of an eye for opening Schlemm's canal.

* * * * *